United States Patent [19]

Blank

[11] 4,105,692

[45] Aug. 8, 1978

[54] PROCESS FOR THE PREPARATION OF BENZENESULPHONYL CHLORIDE

[75] Inventor: Heinz Ulrich Blank, Odenthal, Germany

[73] Assignee: Bayer Aktiengesellschaft, Leverkusen, Germany

[21] Appl. No.: 817,464

[22] Filed: Jul. 19, 1977

[30] Foreign Application Priority Data

Aug. 5, 1976 [DE] Fed. Rep. of Germany ....... 2635281

[51] Int. Cl.$^2$ ........................................... C07C 143/26
[52] U.S. Cl. .............................................. 260/543 R
[58] Field of Search ................................. 260/543 R

[56] References Cited

U.S. PATENT DOCUMENTS 3,701,806 10/1972 Keogh et al. .................... 260/543 R

OTHER PUBLICATIONS

Monatsheft fur Chemie, vol. 34, p. 570 (1913).

*Primary Examiner*—Gerald A. Schwartz
*Attorney, Agent, or Firm*—Burgess, Dinklage & Sprung

[57] ABSTRACT

An improvement in the process for preparing benzenesulphonic acid chloride by reacting benzenesulphonic acid with thionyl chloride, the improvement residing in carrying out the process in the presence of a sulphonating agent.

18 Claims, No Drawings

PROCESS FOR THE PREPARATION OF BENZENESULPHONYL CHLORIDE

The invention relates to a process for the preparation of benzenesulphonic acid chloride.

It is known, that, in general, by reacting benzenesulphonic acid with thionyl chloride, in excess, at the boiling point no benzenesulphonic acid chloride but almost exclusively benzenesulphonic acid anhydride is obtained (Monatsheft für Chemie, vol. 34 (1913), p. 570).

SUMMARY OF THE INVENTION

It has now been found that benzenesulphonic acid chloride is obtained by reacting benzenesulphonic acid with thionyl chloride when the reaction of benzenesulphonic acid with thionyl chloride is carried out in the presence of a sulphonating agent.

Sulphonating agents which can be used are, for example, sulphuric acid, sulphur trioxide, chlorosulphonic acid, fluorosulphonic acid or mixtures thereof; sulphuric acid, sulphur trioxide and chlorosulphonic acid or mixtures thereof, for example oleum, are preferably used.

Generally, sulphonating agents which can be used are electrophilic sulphonating agents (for example Cerfontain, Mechanistic Aspects in Aromatic Sulfonation and Desulfonation, Interscience Publishers, 1968, p. 1–11).

In general, up to 20% by weight, preferably 0.1 to 15.0% by weight and especially 0.25 to 5.0% by weight of sulphonating agent are employed, the amount of sulphonating agent being relative to the amount of benzenesulphonic acid employed; in general, in the case of small amounts of sulphonating agent, the rate of reaction increases with an increasing amount of sulphonating agent.

It is also possible to use more than 20% by weight of a sulphonating agent, but in general this brings no advantage.

The sulphonating agent, optionally in a mixture with a reactant, can be both initially introduced at the start of the reaction or added during the reaction in portions or all at once.

In general, the process according to the invention is carried out in the temperature range between about 0° to 170° C, preferably between 20° and 160° C and especially between 50° and 150° C.

In general, thionyl chloride is used in an excess above the stoichiometrically required amount of one mol of thionyl chloride per mol of benzenesulphonic acid.

The excess can be up to 10 mols of thionyl chloride per mol of benzenesulphonic acid. A larger excess can also be used, it being possible for the excess thionyl chloride simultaneously to serve as the solvent.

1.1 to 5.0 mols, and especially 1.2 to 2.5 mols, of thionyl chloride can advantageously be used per mol of benzenesulphonic acid.

The excess thionyl chloride can serve as the solvent at the same time, but the process according to the invention can also be carried out in the presence of a solvent or diluent which is inert under the reaction conditions. Such solvents or diluents which can be used are sulphur dioxide and sulphuryl chloride, hydrocarbons and halogenohydrocarbons, in particular alkanes and halogenoalkanes, such as chloroform, carbon tetrachloride, methylene chloride, di-, tri- and tetra-chloroethylene, di-, tri- tetra-and penta-chloroethane, 1,1,2-trichloro-1,2,2-trifluoroethane and tetrafluoroethylene.

The end product of the process according to the invention, that is to say benzenesulphonic acid chloride, can also be used as the solvent, and likewise diphenyl sulphone.

In this procedure it is not necessary to use specially purified thionyl chloride. For economic reasons also, it is advantageous to employ commercially available thionyl chloride.

The benzenesulphonic acid can be employed as the starting compound for the process according to the invention both in the pure form and as the crude product.

Depending on the specific preparation process, possible impurities in the crude benzenesulphonic acid are, for example: water, benzenedisulphonic acid, diphenyl sulphone, diphenyl sulphone-sulphonic acid, benzenesulphonic acid anhydride and benzene as unreacted starting material. Furthermore, the benzenesulphonic acid can contain residues of sulphonating agent, such as sulphur trioxide, sulphuric acid and chlorosulphonic acid, and also of those additives which were used during its preparation to prevent sulphone formation, such as acetic acid, phosphorus oxychloride, phosphoric acid, phosphoric acid esters, benzoic acid and sulphates. The amount and the ratio of the individual impurities can vary, depending on the preparation process.

Benzenesulphonic acid which has been prepared by reacting benzene with sulphur trioxide in a known manner is preferably used as the starting material for the process according to the invention. For this preparation, benzene can be reacted with sulphur trioxide at temperatures between about 10° to 100° C, preferably 25° to 65° and especially 40° to 60° C, under normal, reduced or increased pressure; preferably under a reduced pressure of 50 to 600 mbars, preferably 100 to 500 and especially 150 to 400 mbars. In general, 0.1 to 1.1, preferably 0.25 to 0.8 and especially 0.3 to 0.7, mols of $SO_3$ are used in this procedure per mol of benzene.

The reaction can be carried out both without a solvent and in the presence of an inert solvent. Furthermore, it is possible to add to the benzene employed 0.1 to 5, in particular 0.2 to 2.5,% by weight of one of the known substances which reduce or prevent the side reaction of diphenyl sulphone formation.

These known processes for the preparation of benzenesulphonic acid by reacting benzene with gaseous $SO_3$ and the additives for reducing the sulphone bond are described, for example, in U.S. Pat. Nos. 2,704,295, 2,831,020, 3,072,618, 3,072,703, 3,133,117, 3,248,413, 3,232,976 and 1,422,564, British Patent Specification No. 791,995, Deutsche Auslegeschrift (Published Specification) No. 1,468,490 and Deutsche Offenlegungsschriften (Published Specifications) Nos. 2,353,918, 2,354,097, 2,019,527, 2,019,250, 1,493,311, 1,443,414 and 1,418,773.

The benzenesulphonic acid thus prepared frequently already contains, as an impurity arising from the preparation, a sulphonating agent in a sufficient amount, such as is required by the process according to the invention. Thus in many cases further addition of sulphonating agent is superfluous.

It is also possible to use, in a similar manner, benzenesulphonic acid which has been prepared by reacting benzene with other sulphonating agents, such as sulphuric acid, oleum or chlorosulphonic acid.

If a crude benzenesulphonic acid still contains relatively large amounts of benzene, from its preparation, as an impurity, it must of course be taken into account that this benzene can be further sulphonated by the sulphonating agent and thus consumes sulphonating agent; this amount of sulphonating agent consumed by the benzene must then be used in addition to the amount of sulphonating agent which, by the process according to the invention, is required and is to be employed.

Of course, one can also use pure benzenesulphonic acid or a benzenesulphonic acid which is purified to such an extent that it contains no further sulphonating agent as an impurity. In this case, a sulphonating agent must be added in the appropriate amount.

The sequence of the bringing together of the three reactants is not critical. It is only necessary that the amount of sulphonating agent corresponding to the amount of benzenesulphonic acid employed is added to the reaction mixture in the course of the reaction.

In one variant, the process according to the invention is carried out by initially introducing thionyl chloride and the chosen amount of sulphonating agent, heating the mixture to the chosen reaction temperature and subsequently adding benzenesulphonic acid at this temperature.

On the other hand, one can also initially introduce thionyl chloride and add benzenesulphonic acid and sulphonating agent simultaneously, either after prior mixing or separately, to the thionyl chloride.

Thus, for example, in the case of the preferred use of a crude benzenesulphonic acid which already contains the corresponding amount of sulphonating agent as an impurity, the sulphonating agent is added, together with benzenesulphonic acid, to the initially introduced thionyl chloride.

It is also possible to initially introduce benzenesulphonic acid, optionally together with sulphonating agent, and to add thionyl chloride at the appropriate temperature.

In this procedure also, instead of adding the sulphonating agent to the benzenesulphonic acid from the beginning, it can be added simultaneously with the thionyl chloride, either as a mixture with this or also separately, it being necessary for the total amount of sulphonating agent to be present in the reaction mixture only after adding the total amount of thionyl chloride.

In a particular variant of the process according to the invention, benzenesulphonic acid and thionyl chloride can also be brought together at room temperature or the reaction temperature, whereupon the abovementioned reaction to give sulphonic acid anhydride already begins and, depending on the temperature and the time up to the addition of the sulphonating agent, a corresponding amount of benzenesulphonic acid anhydride is formed. The corresponding amount of sulphonating agent is subsequently added to the reaction mixture, it not being necessary for this addition to be made immediately, but it being possible for the addition also to be made when a relatively large proportion of the benzenesulphonic acid has already reacted to give benzenesulphonic acid anhydride. According to this variant, it is thus also possible to employ benzenesulphonic acid anhydride instead of benzenesulphonic acid.

For the process according to the invention it is not that essential that the reaction between benzenesulphonic acid and thionyl chloride already begins in the presence of sulphonating agents, but that it is brought to completion in the presence of the corresponding amount of sulphonating agent.

Thus, by the process according to the invention, benzenesulphonic acid anhydride can also optionally serve as the starting material instead of benzenesulphonic acid.

If thionyl chloride is initially introduced, one can add the benzenesulphonic acid, in the solid or liquid form, in the molten state or dissolved in an inert solvent, to the thionyl chloride at the chosen reaction temperature all at once, in portions, or continuously. Of course, if necessary, it is also possible to melt the benzenesulphonic acid at a temperature which is higher than the chosen reaction temperature in order to be able to add it in the liquid form.

If benzenesulphonic acid is initially introduced, it can be advantageous to choose the reaction temperature so that the benzenesulphonic acid is present as a melt. If the reaction is to be carried out at a lower temperature, it can be advantageous to do so in the presence of an inert solvent so that the benzenesulphonic acid is at least partially dissolved.

It can also be advantageous to carry out the process according to the invention by initially introducing thionyl chloride. This procedure can be advisable because thionyl chloride is a liquid even in the lower temperature range of the process according to the invention and the use of an inert solvent is thus superfluous in every case.

In a preferred process, liquid or gaseous thionyl chloride is added, in the presence of a sulphonating agent, to molten benzenesulphonic acid at temperatures from the melting point of benzenesulphonic acid up to 170° C, preferably from 60° to 160° C and especially from 65° up to 150° C.

Of course, the sulphonating agent, in the chosen amount, as indicated above, can be either added to the thionyl chloride before the reaction or mixed with the benzenesulphonic acid or contained in this as an impurity. The separate addition of sulphonating agent in the corresponding amount simultaneously with or after the second reactant is also possible, as described above.

According to the reaction equation indicated below

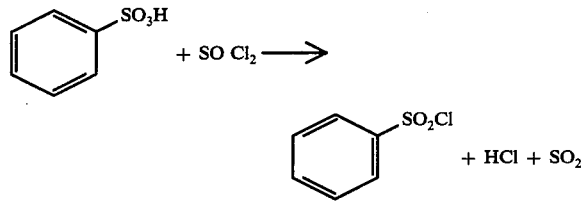

hydrogen chloride and sulphur dioxide, which can be removed, separated and optionally further used, in a known manner, are formed as by-products in the reaction.

After the reaction has ended, which can be determined by the fact that evolution of gas has ceased or by means of known analytical methods, excess thionyl chloride, if appropriate, is separated off, for example by distillation, and the benzenesulphonic acid chloride is isolated. It can be used either directly or purified in a known manner, for example by crystallisation or distillation.

The reaction mixture is advantageously worked up by distillation, in general, excess thionyl chloride, if appropriate, being initially distilled off under normal pressure or under a reduced pressure down to about 10 mbars and the benzenesulphonic acid chloride then being isolated by fractional distillation under reduced pressure, preferably in the range from 0.1 to 10 mbars.

The first and last runnings thereby obtained, and, if appropriate, the residue, can contain sulphonating agent and can be used as the sulphonating agent in the corresponding amount in a new batch or, if the process according to the invention is carried out continuously, can be partially or completely recycled to the reaction.

If the benzenesulphonic acid used contained high-boiling impurities, such as diphenyl sulphone, these turn up in the distillation residue and can optionally be isolated from this and put to a separate use.

Unreacted benzenesulphonic acid, if appropriate, can also be in the distillation residue, as such or in the form of its anhydride, and, if appropriate after separating off diphenyl sulphone and other impurities which cannot be reacted to benzenesulphonic acid chloride, can be used again as the starting material for the process according to the invention or can be recycled to the reaction.

In general, the process according to the invention is carried out under normal pressure or a slight excess pressure, so that the boiling point of the reaction mixture is at or above the reaction temperature.

One can also carry out the process under reduced pressure, so that the gaseous by-products sulphur dioxide and hydrogen chloride can escape more rapidly.

However, the pressure in itself is not essential for carrying out the process according to the invention.

The process according to the invention can be carried out both discontinuously and continuously.

The procedure followed when carrying out the process discontinuously is advantageously to introduce only a small portion of the benzenesulphonic acid into the thionyl chloride at the start of the reaction and to add the rest batchwise or continuously at the same rate at which the formation of the sulphonic acid chloride takes place. In this procedure, the formation of the sulphonic acid chloride can be followed manometrically by means of the formation of hydrogen chloride and sulphur dioxide linked therewith, or by known analytical methods.

The gaseous hydrogen chloride and sulphur dioxide, which are formed as a by-product, can entrain thionyl chloride in the gaseous or liquid state. It can be advantageous to pass this off-gas through optionally only partially liquid benzenesulphonic acid, which optionally contains sulphonating agent, in order to recover or react the thionyl chloride and optionally simultaneously to use its heat for melting and pre-warming the benzenesulphonic acid.

This method is particularly advisable for the continuous method.

The process according to the invention is preferably carried out continuously. For example, the process can be carried out in a loop reactor into which thionyl chloride and benzenesulphonic acid containing sulphonating agent are metered in at two inlets in rapid succession, whilst the reaction mixture is removed at an outlet point positioned just upstream from the inlets. Hydrogen chloride and sulphur dioxide can be drawn off together with the reaction mixture or also as a gas at other points of the loop reactor via let-down valves. In the continuous method, a countercurrent process is preferably carried out. In such a variant of carrying out the process continuously, the process can be carried out, for example, in a bubble column according to the countercurrent principle, liquid benzenesulphonic acid being fed in at the head of the column and liquid or gaseous thionyl chloride being fed in in the lower region of the column. In this procedure the sulphonating agent can be either preferably mixed previously with the benzenesulphonic acid or simultaneously fed in in a separate stream. However, it can also be fed in together with the thionyl chloride, mixed with the thionyl chloride or separately.

In this procedure, the bubble column can also be provided with intermediate trays and can be operated in the various regions of the column at various reaction temperatures.

The removal of the reaction product usually takes place in the lower region of the column, whilst the benzenesulphonic acid is led to the upper region of the column.

Furthermore, the reaction by the process according to the invention can also be carried out in a cascade of reaction kettles.

The reaction mixture removed is worked up discontinuously or continuously, for example by distillation, and excess thionyl chloride as well as unreacted benzenesulphonic acid, if appropriate, is recycled to the reaction.

In the above, the addition of sulphonating agent was not mentioned in some cases since this can either already be contained in the benzenesulphonic acid as an impurity, or on the other hand its addition has already been described in detail above, so that a repetition was superfluous at this point.

By a particularly preferred variant of the process according to the invention, benzenesulphonic acid is prepared in a first process stage by reacting benzene with up to 0.8 mol of sulphur trioxide per mol of benzene, the unreacted benzene is then separated off and the crude benzenesulphonic acid thus obtained is used as the starting material for the process according to the invention. This variant of the process according to the invention is thus so advantageous because the crude benzenesulphonic acid thus obtained is particularly simple to prepare and, as already described, is particularly suitable as the starting material for the process according to the invention because of its content of sulphonating agent as an impurity, which is in general already sufficient, since in general a further addition of sulphonating agent is not necessary and thus appropriate metering and mixing devices are also superfluous, which simplifies the apparatus aspect of the process.

It is surprising that the reaction of benzenesulphonic acid with thionyl chloride, in which benzenesulphonyl chloride is formed only to a minor extent and benzenesulphonic acid anhydride is mainly formed, proceeds uniformly in the presence of sulphonating agents so that benzenesulphonyl chloride is exclusively formed in high yields.

Compared with the known preparation of benzenesulphonic acid chloride by reacting benzene with chlorosulphonic acid (Ullmann's Enzyklopädie der Technischen Chemie (Ullmann's Encyclopaedia of Industrial Chemistry), 4th edition, vol. 8 (1974), p. 420) the process according to the invention has, in particular, the advantage that the reaction mixture can be worked up by distillation immediately and that the dilute acid problem which exists according to the state of the art is avoided.

Mainly gaseous by-products are formed, that is to say hydrogen chloride and sulphur dioxide, whilst in the known processes about 18% of theory of benzenesulphonic acid and 5 to 7% of theory, relative to benzene, of diphenyl sulphone as well as the associated reaction products hydrogen chloride and sulphuric acid are obtained. In particular, the recovery and recycling of the chlorosulphonic acid, which is used in excess, is a problem which has not yet been solved, so that it must be decomposed with water and as dilute acid, together with the benzenesulphonic acid and the sulphuric acid, which must be worked up both adversely affects the economy of the process and causes great problems of effluent removal and environmental protection:

According to the state of the art, about 6 tonnes of dilute acid (about 0.2 tonne of benzenesulphonic acid, 1.5 tonnes of sulphuric acid and 0.3 tonne of hydrochloric acid) are obtained per tonne of benzenesulphonyl chloride.

In addition, in the process according to the state of the art a benzene-containing reaction off-gas is obtained which, in addition to the effluent problem mentioned, also causes off-gas problems insofar as on the off-gas side the benzene must also be removed. In addition to the dilute acid problem, a corresponding waste air problem is also avoided in the process according to the invention.

Its particular technical and ecological advance, in particular, is thus in the field of environmental protection.

However, the process according to the invention also has the advantage that the yield, relative to benzenesulphonic acid, is very high and virtually quantitative. In carrying out the process according to the invention, also virtually only the amount of thionyl chloride which is equimolar to that of benzenesulphonic acid is consumed, in spite of the fact that it is in general employed in excess, whilst the excess can be recovered or, when the process is carried out continuously, can be circulated and only the amount of thionyl chloride consumed must be replaced. The sulphonating agent employed can also be substantially recovered and employed again.

EXAMPLES

The apparatus used in the examples which follow consisted of a 1 liter flask which was provided with an internal thermometer, stirrer, reflux condenser and a heatable dropping funnel. The internal temperature of the flask could be kept constant to within a few degrees by means of controllable heating, so that the temperature of the reaction mixture varied only about 1° to 3° C from the value indicated in the examples which follow.

The benzenesulphonic acid used had the particular purity indicated in % and contained, as impurities, mainly diphenyl sulphone, water and traces of sulphuric acid.

The amount of sulphonating agent is indicated in grams in each case, the data in mols and % by weight relative to benzenesulphonic acid following afterwards in the bracket.

Example 1

A mixture of 238 g (2 mols) of thionyl chloride and 5 g (0.063 mol, 3.2%) of sulphur trioxide is initially introduced into the flask and warmed to 60° C. 158 g (1.0 mol) of benzenesulphonic acid (98.1% pure) are added dropwise at this temperature in the course of 2 hours, whereupon vigorous evolution of gas begins.

After the addition has ended, the mixture is subsequently stirred for a further 2 hours until the evolution of gas has ended and excess thionyl chloride is then distilled off under normal pressure.

184 g of crude product remain, which are distilled under a reduced pressure of 2.0 to 0.7 mm Hg; this gives: 3.4 g of first runnings between 72° to 78° C, 174.0 g of main runnings at about 89° C and 2.3 g of distillation residue.

The main runnings consist of benzenesulphonic acid chloride with a purity of 99.7%, corresponding to a yield of 100% of theory, relative to benzenesulphonic acid (100% pure) employed.

Example 2

238 g of thionyl chloride are initially introduced at an internal temperature of 60° C. A mixture of 158 g (1.0 mol) of benzenesulphonic acid (98.5% pure) and 5 g (0.043 mol, 3.2%) of chlorosulphonic acid is added dropwise from the dropping funnel in the course of 2 hours.

The mixture is then subsequently stirred for a further three and a half hours at the same temperature until the evolution of gas has ended and excess thionyl chloride is then distilled off under normal pressure.

This gives 189 g of crude product, and distillation thereof under a reduced pressure of between 2.5 and 1.2 mm Hg gives 7.3 g of first runnings between 40° and 78° C, 165.0 g of main runnings between 85° to 89° C, 1.6 g of last runnings between 119° and 145° C and 6.5 g of distillation residue.

The main runnings are benzenesulphonic acid chloride of 99.6% purity, corresponding to a yield of 94.4% of theory, relative to benzenesulphonic acid (100% pure).

EXAMPLE 3

238 g of thionyl chloride are initially introduced at an internal temperature of 60° C and a mixture of 158 g (1.0 mol) of benzenesulphonic acid and (98.5% pure) and 2.5 g (0.026 mol, 1.6%) of $H_2SO_4$ is added dropwise in the course of 2 hours, whilst stirring.

The mixture is then subsequently stirred for a further 3½ hours at the same temperature until the evolution of gas has ended and excess thionyl chloride is then distilled off under normal pressure.

This gives 177 g of crude product, and distillation thereof under a reduced pressure of 1.2 mm Hg gives 3.1 g of first runnings between 80° and 87° C, 126.3 g of main runnings at 87° C, 3.7 g of last runnings between 100° and 150° C and 41 g of distillation residue.

The main runnings are benzenesulphonic acid chloride of 100% purity, corresponding to a yield of 72% of theory, relative to benzenesulphonic acid (100% pure).

The distillation residue predominantly consists of unreacted benzenesulphonic acid.

EXAMPLE 4

A mixture of 158 g (1.0 mol) of benzenesulphonic acid (98.5% pure) and 7.5 g (0.075 mol, 4.7%) of $H_2SO_4$ is added to 238 g of thionyl chloride at an internal temperature of 60° C in the course of 2 hours, whilst stirring. The mixture is subsequently stirred for a further 3½ hours at the same temperature until the evolution of gas has ended and then excess thionyl chloride is distilled off under normal pressure.

188 g of crude product are thus obtained, and distillation thereof under a reduced pressure of 1.0 mm Hg gives 32.2 g of fraction I between 85° and 86° C, 143.9 g of fraction II between 86° and 90° C, 2.6 g of last runnings at a temperature rising at 94° C and 1.0 g of distillation residue.

Fraction I was benzenesulphonic acid chloride of 98.6% purity and fraction II was benzenesulphonic acid chloride of 99.3% purity.

The yield of benzenesulphonic acid chloride (fraction I + fraction II) is about 100% of theory, relative to benzenesulphonic acid (100% pure).

If the above experiment is repeated but 15 g (0.15 mol, 9.4%) of $H_2SO_4$ are used instead of 7.5 g of $H_2SO_4$, the reaction has already ended after a subsequent stirring time of 2 hours.

After the working up, described above, of the reaction mixture, benzenesulphonic acid chloride is likewise obtained in quantitative yield.

EXAMPLE 5 (Comparison example)

158 g of benzenesulphonic acid (98.5% pure) were added dropwise to 238 g of thionyl chloride at 60° C in the course of about 2 hours, whilst stirring. The mixture was stirred for a further 2 hours at the same temperature until the evolution of gas had ended and the excess thionyl chloride was then distilled off under normal pressure.

This gives 179 g of residue, and distillation thereof under a reduced pressure of 1.0 mm Hg gives 37.9 g of fraction I between 88° and 100° C, 9.3 g of fraction II between 100° and 140° C and 132.0 g of distillation residue.

The content of benzenesulphonic acid chloride in fraction I corresponds to a yield of 22% of theory, relative to benzenesulphonic acid (100% pure).

EXAMPLE 6 (Comparison example)

238 g of thionyl chloride were metered into 158 g of benzenesulphonic acid (98.5% pure) at 60° C in the course of about 2 hours, whilst stirring. The mixture was stirred for a further 2 hours at the same temperature until the evolution of gas had ended and the excess thionyl chloride was then distilled off under normal pressure.

Fractional distillation of the residue under a reduced pressure of 1.0 mm Hg gives 42.9 g of fraction I between 88° and 100° C, 8 g of fraction II between 100° and 135° C, 66.7 g of fraction III between 135° and 165° C and 100 g of distillation residue.

The content of benzenesulphonic acid chloride in fraction I corresponds to a yield of 24% of theory, relative to benzenesulphonic acid (100% pure).

EXAMPLE 7 (Comparison example)

238 g of thionyl chloride and 158 g of benzenesulphonic acid (98.5% pure) are mixed at room temperature and warmed to 60° C for 5 hours until the evolution of gas has ended.

Excess thionyl chloride is then distilled off under normal pressure and the residue is distilled under a reduced pressure of 1.0 mm Hg; this gives 39.6 g of fraction I between 85° and 100° C, 10.6 g of fraction II between 100° and 170° C, 82.5 g of fraction III between 170° and 177° C and 38.1 g of residue.

The content of benzenesulphonic acid chloride in fraction I corresponds to a yield of 22% of theory, relative to benzenesulphonic acid (100% pure).

EXAMPLE 8

(a) Benzenesulphonic acid

The apparatus used consisted of a vertical reaction tube 6 cm in diameter and 40 cm in height, surmounted by a reflux condenser. A gas inlet tube, which ended in a horizontal frit of about 4 cm in diameter was introduced at a height of 4 cm above the bottom of the reaction tube; at a height of 20 cm above the bottom of the reaction tube was an internal thermometer introduced through a ground-glass joint positioned at the side. The contents of the reaction tube could be stirred with the aid of a magnetic stirrer.

624 g (8 mols) of benzene and 8 g of orthophosphoric acid were filled into the apparatus described above and heated to 40° C, whilst stirring.

320 g of liquid $SO_3$ were introduced dropwise into a vaporiser, heated to 60° C, in the course of one hour and the $SO_3$ vapour was passed into the benzene via a safety vessel through the gas inlet tube and the attached frit. Simultaneously, the pressure downstream of the reflux condenser in the gas outlet tube was adjusted to about 300 mbars in the customary manner and it was thereby achieved that a uniform stream of gaseous $SO_3$ was sucked into the reaction mixture in fine distribution through the gas inlet frit, the liquid $SO_3$ being introduced into the vaporiser only at the rate at which it left the latter in the gaseous state.

The temperature, measured with the internal thermometer, was kept at 45° ± 5° C during the reaction; the cooling temperature of the reflux condenser was adjusted so that benzene which evaporated was condensed again.

After a reaction time of 1 hour, 938 g of a solution of benzenesulphonic acid in benzene was obtained. Excess benzene was distilled off in a rotary evaporator, finally at a bath temperature of 80° C and under a pressure of 10 mbars.

631.4 g of benzenesulphonic acid with a purity corresponding to the analysis data which follow were obtained.

Analysis: 4.13% of sulphuric acid 5.1% of diphenyl sulphone <0.25% of diphenyl sulphone-monosulphonic acid <0.25% of diphenyl sulphone-disulphonic acid <0.25% of benzenedisulphonic acid Remainder: benzenesulphonic acid.

(b) Benzenesulphonyl chloride

The same apparatus was used as in Examples 1 to 7. 298 g. (2.5 mols) of thionyl chloride was initially introduced into the flask and heated to 60° C. 158 g (1 mol) of benzenesulphonic acid (prepared as described under (a)), warmed to 60° C, were added dropwise from the dropping funnel in the course of 3 hours, whilst stirring. The reaction products hydrogen chloride and sulphur dioxide escaped in the gaseous state through the reflux condenser. After the addition of benzenesulphonic acid had ended, the mixture was subsequently stirred for a further 2 hours at 60° C until the evolution of gas had ended.

Excess thionyl chloride was then evaporated off in a rotary evaporator at 60° C and under a waterpump vacuum.

The liquid residue was distilled over a distillation bridge; 160.1 g of benzenesulphonyl chloride (purity 99.2%) were obtained as a colourless distillate at a head temperature of 86° C/1.0 mm Hg; this corresponds to a yield of 99% of theory, relative to benzenesulphonic acid (100% pure).

EXAMPLE 9

158 g of benzenesulphonic acid (98.1% pure) and 5 g (0.05 mol, 3%) of sulphuric acid are initially introduced at 60° C. 179 g (1.5 mols) of thionyl chloride are added dropwise at this temperature in the course of 4 hours through a dropping funnel with pressure compensator, dipping into the reaction mixture. The mixture is then subsequently stirred for a further 4 hours until the evolution of gas has ended and the excess thionyl chloride is then distilled off under a waterpump vacuum.

This gives 180 g of crude product, which is distilled under a reduced pressure of between 1.7 and 0.6 mm Hg; this gives 3.4 g of first runnings between 65° and 80° C, 172 g of main runnings at 86° C and 3.7 g of distillation residue.

The main runnings consist of benzenesulphonic acid chloride with a purity of 99.8%, corresponding to a yield of 99.2% of theory, relative to benzenesulphonic acid (100% pure) employed.

EXAMPLE 10

158 g of benzenesulphonic acid (98.1% pure), 5 g (0.05 mol, 3%) of sulphuric acid and 595 g (5 mols) of thionyl chloride are mixed at room temperature, whereupon evolution of gas already takes place. The mixture is warmed to 60° C and stirred for 4 hours at this temperature until the evolution of gas has ended.

The excess thionyl chloride is then distilled off under a waterpump vacuum. This gives 183 g of crude product, and distillation thereof under 3.4 to 1.1 mm Hg gives 3.0 g of first runnings between 65° and 90° C, 175 g of main runnings at 90° and 80° C (3.4 to 1.1 mm Hg) and 2.5 g of distillation residue.

The main runnings are benzenesulphonyl chloride of 99.8% purity, corresponding to a yield of 100% of theory, relative to benzenesulphonic acid (100% pure).

EXAMPLE 11

158 g of benzenesulphonic acid (98.1% pure) and 7.5 g (0.075 mol, 4.7%) of sulphuric acid are mixed at 60° C, the mixture is warmed to 120° C and 214 g (1.8 mols) of thionyl chloride are added dropwise at this temperature in the course of 2 hours, whilst stirring, through a dropping funnel with pressure compensator, dipping into the reaction mixture. After about 120 g of thionyl chloride have been metered in, the temperature of the mixture falls to about 110° C during the addition of the remaining thionyl chloride, whilst the reaction mixture boils under reflux. The mixture is subsequently stirred for a further 90 minutes until the evolution of gas has ended and excess thionyl chloride is then distilled off under a waterpump vacuum.

This gives 187 g of crude product, and distillation thereof under a reduced pressure of 2.5 to 1.5 mm Hg gives 4.0 g of first runnings between 30° and 89° C, 174 g of main runnings between 94° and 95° C and 4.7 g of distillation residue.

The main runnings consist of benzenesulphonic acid chloride with a purity of 99.7%, corresponding to a quantitative yield, relative to benzenesulphonic acid (100% pure).

EXAMPLE 12

158 g of benzenesulphonic acid (98.1% pure) and 7.5 g of sulphuric acid are mixed at 60° C, the mixture is warmed to 90° C and 214 g of thionyl chloride are added dropwise at this temperature in the course of 2 hours, whilst stirring, through a dropping funnel with pressure compensator, dipping into the reaction mixture. The mixture is subsequently stirred for a further 2½ hours at 90° C until the evolution of gas has ended and the thionyl chloride is then distilled off under a waterpump vacuum.

190 g of crude product remain, which are distilled under a reduced pressure of 2.8 to 2.0 mm Hg. This gives 6.9 g of first runnings between 59° and 92° C, 175 g of main runnings between 96° and 101° C and 4.4 g of residue.

The main runnings consist of benzenesulphonic acid chloride with a purity of 99.4%, which corresponds to a quantatitave yield, relative to benzenesulphonic acid (100% pure).

EXAMPLE 13

238 g of thionyl chloride and 158 g of benzenesulphonic acid (98.1% pure) are mixed at room temperature and the mixture is warmed to 60° C and stirred for about 5 hours at this temperature until the evolution of gas has ended.

After the evolution of gas has ended, 7.5 g of sulphuric acid are added. Renewed vigorous evolution of gas takes place immediately, which, whilst further stirring at 60° C, has ended after about 5½ hours.

Excess thionyl chloride is then distilled off under a waterpump vacuum.

186.4 g of crude product remain, which are distilled under a reduced pressure of 4.4 to 4.0 mm Hg; this gives 4.8 g of first runnings between 80° and 85° C, 175.1 g of main runnings between 104° and 107° C and 2.2 g of distillation residue.

The main runnings consist of benzenesulphonic acid chloride with a purity of 99.7%, corresponding to a yield of 100% of theory, relative to benzenesulphonic acid (100% pure) employed.

EXAMPLE 14

158 g (1.0 mol) of molten benzenesulphonic acid, which contains the following impurities: 0.03% by weight of $H_2O$, 2.7% by weight of sulphuric acid, 6.5% of diphenyl sulphone and 0.3 to 0.4% by weight of benzenedisulphonic acid, are added dropwise to 238 g (2.0 mols) of thionyl chloride at 40° C in the course of 3 hours, whilst stirring. The mixture is further stirred at this temperature for 11 hours until the evolution of gas has ended.

Excess thionyl chloride is then distilled under normal pressure and the residue of 166 g is subsequently distilled under a reduced pressure of 15 mm Hg. This gives 69.4 g of distillate between 110° and 120° C and 86.3 g of distillation residue.

The distillate is benzenesulphonic acid chloride and corresponds to a yield of 44% of theory, relative to benzenesulphonic acid (100% pure) employed.

EXAMPLE 15

158 g of the same molten benzenesulphonic acid which was used in Example 14 are added dropwise to 238 g of thionyl chloride at 50° C in the course of 3 hours, whilst stirring.

The mixture is further stirred at the same temperature for 8 hours until the evolution of gas has ended and the excess thionyl chloride is then distilled off under normal pressure.

The resulting residue of 180 g is distilled under a reduced pressure of about 10 mm Hg and gives 158 g of distillate between 105° and 115° C and 12 of residue.

The distillate is pure benzenesulphonic acid chloride, corresponding to a yield of 99% of theory, relative to benzenesulphonic acid (100% pure) employed.

EXAMPLE 16

119 g (1.0 mol) of thionyl chloride are added dropwise to 158 g of the benzenesulphonic acid, which was used in Example 14, at 60° C in the course of 4 hours, whilst stirring. The mixture is then subsequently stirred at this temperature for a further 2 hours until the evolution of gas has ended.

The reaction mixture is then distilled under reduced pressure, some thionyl chloride being distilled off under about 100 mm Hg.

The residue of 175 g is then distilled under about 10 mm Hg and this gives 106 g of distillate between 105° and 112° C and 57 g of residue.

The distillate is benzenesulphonic acid chloride of 99.3% purity, corresponding to a yield of 66% of theory, relative to benzenesulphonic acid (100% pure).

EXAMPLE 17

149 g (1.25 mols) of thionyl chloride are added dropwise to 158 g of benzenesulphonic acid, of the composition given in EXAMPLE 14, at 60° C in the course of 4 hours, whilst stirring. The mixture is then further stirred at this temperature until the evolution of gas has ended.

Some excess thionyl chloride is stripped off under a reduced pressure of about 10 mm Hg and the residue is then distilled under about 6 mm Hg; this gives 160.1 g of distillate at about 103° and 12.3 g of residue.

The distillate is benzenesulphonic acid chloride with a purity of 99.1%, corresponding to a yield of 99% of theory, relative to benzenesulphonic acid (100% pure).

EXAMPLE 18

158 g of benzenesulphonic acid (97.4% pure), which contain 1.6% of sulphuric acid, 0.4% of diphenyl sulphone and 0.6% of water, are warmed to 150° C and 238 g of thionyl chloride are added dropwise at this temperature in the course of 2 hours, whilst stirring, through a dropping funnel with pressure compensator, dipping in the reaction mixture. After about 140 g of thionyl chloride have been added, the temperature of the mixture falls to about 105° C during the addition of the remaining thionyl chloride, whilst the reaction mixture boils under reflux. The mixture is subsequently stirred for a further 60 minutes and excess thionyl chloride is then distilled off under a waterpump vacuum.

This gives 173 g of crude product, and distillation thereof under about 3 mm Hg gives 161 g of main runnings (97°–99° C) and 6.4 g of residue.

The main runnings consist of benzenesulphonic acid chloride with a purity of 99.9%, corresponding to a yield of 93.5% of theory, relative to 100% pure benzenesulphonic acid.

EXAMPLE 19

158 g of benzenesulphonic acid (99.5% pure) are added dropwise to a mixture of 238 g (2 mols) of thionyl chloride and 32 g (0.4 mol; 20%) of sulphur trioxide 20° C in the course of 4 hours, whilst stirring. The mixture is further stirred for 6 hours and excess thionyl chloride is then distilled off under a waterpump vacuum.

This gives a 208.2 g of crude product, which is distilled under 5 to 1.4 mm Hg; this gives 9.4 g of first runnings I between 40° and 65°/5 mm Hg, 29.5 g of first runnings II between 65° and 84°/5 to 2.7 mm Hg, 147.3 g of main runnings at about 85°/1.5 mm Hg, 2.8 g of last runnings at about 120°/1.4 mm Hg and 4.9 g of residue.

The main runnings consist of benzenesulphonic acid chloride with a purity of 99.3%, corresponding to a yield of 83% of theory, relative to benzenesulphonic acid (100% pure) employed.

EXAMPLE 20

158 g of benzenesulphonic acid (99.5% pure), which contain 0.14% of sulphuric acid and 0.38% of diphenyl sulphone, are mixed with 0.16 g (0.002 mol; 0.1%) of sulphuric acid and the mixture is warmed to 120° C. 238 g of thionyl chloride are added dropwise in the course of 2 hours. After about 130 g of thionyl chloride have been added, the temperature of the mixture falls to about 105° C during the addition of the remaining thionyl chloride, whilst the reaction mixture boils under reflux. The mixture is subsequently stirred for a further 6 hours and excess thionyl chloride is then distilled off under a waterpump vacuum.

This gives 178 g of crude product, and distillation thereof under about 8 mm Hg gives 154 g of main runnings between 115° and 118° C and 25 g of residue.

The main runnings consist of benzenesulphonic acid chloride with a purity of 99.7%, corresponding to a yield of 87% of theory, relative to benzenesulphonic acid (100% pure) employed.

EXAMPLE 21

158 g of the benzenesulphonic acid used in Example 20 and 1.6 g (0.02 mol, 1%) of sulphuric acid are heated together to 120° C and 238 g of thionyl chloride are added in the course of 2 hours, whilst stirring. After about 140 g of thionyl chloride have been added, the temperature of the mixture falls to about 105° C during the addition of the remaining thionyl chloride, whilst the reaction mixture boils under reflux. The mixture is subsequently stirred for a further 5 hours and excess thionyl chloride is then distilled off under a waterpump vacuum. This gives 183 g of crude product, and distillation thereof under about 7 mm Hg gives 1.3 g of first runnings (92°), 171 g of main runnings (110°–113°) and 2.5 g of residue.

The main runnings consist of benzenesulphonic acid chloride of 99.6% purity, corresponding to a yield of 97% of theory, relative to benzenesulphonic acid (100% pure).

What is claimed is:

1. In a process for the preparation of benzenesulphonic acid chloride by contacting benzenesulphonic acid with thionyl chloride, the improvement which comprises carrying out the process in the presence of an electrophilic sulphonating agent.

2. A process according to claim 1 wherein the sulphonating agent is selected from the group consisting of sulphuric acid, sulphur trioxide, chlorosulphonic acid and mixtures thereof.

3. A process according to claim 1 wherein the sulphonating agent is present in the reaction mixture in an amount up to 20% by weight, based upon the weight of benzenesulphonic acid.

4. A process according to claim 1 wherein liquid thionyl chloride is added to molten benzenesulphonic acid at temperatures from the melting point of benzenesulphonic acid up to 170° C.

5. A process according to claim 1 wherein gaseous thionyl chloride is added to molten benzenesulphonic acid at temperatures from the melting point of benzenesulphonic acid up to 170° C.

6. A process according to claim 1 wherein the benzenesulphonic acid is one obtained by reacting 1 mol of benzene with up to 0.8 mol of sulphur trioxide and thereafter separating off excess benzene.

7. A process according to claim 1 wherein thionyl chloride and the sulphonating agent are introduced into a reaction zone heated therein and benzenesulphonic acid is thereafter introduced into said reaction zone.

8. A process according to claim 1 wherein thionyl chloride is initially introduced into the reaction zone and thereafter benzenesulphonic acid and sulphonating agent are added thereto.

9. A process according to claim 1 wherein to a reaction zone containing benzenesulphonic acid there is added the sulphonating agent and thionyl chloride simultaneously.

10. A process according to claim 1 wherein benzenesulphonic acid and thionyl chloride are heated in a reaction zone and thereafter sulphonating agent is added thereto.

11. A process according to claim 1 wherein the reaction is carried out at a temperature between 0° and 170° C.

12. A process according to claim 1 wherein the process is carried out at a temperature between 20° and 160° C.

13. A process according to claim 1 wherein the process is carried out at a temperature of 50° to 150° C.

14. A process according to claim 1 wherein thionyl chloride is employed in an amount up to 10 mols of thionyl chloride per mol of benzene sulphonic acid.

15. A process according to claim 1 wherein thionyl chloride is present in an amount of 1.1 to 5.0 mols per mol of benzenesulphonic acid.

16. A process according to claim 1 wherein thionyl chloride is present in an amount of 1.2 to 2.5 mols of thionyl chloride per mol of benzenesulphonic acid.

17. A process according to claim 1 wherein the sulphonating agent is present in an amount of 0.1 to 50% by weight based upon the weight of benzenesulphonic acid.

18. A process according to claim 1 wherein the sulphonating agent is present in an amount of 0.25 to 5.0% by weight based upon the weight of benzenesulphonic acid.

* * * * *